United States Patent [19]

Honkonen

[11] Patent Number: 5,545,681
[45] Date of Patent: Aug. 13, 1996

[54] PH-MODIFIED POLYMER COMPOSITIONS WITH ENHANCED BIODEGRADABILITY

[75] Inventor: Robert S. Honkonen, Cincinnati, Ohio

[73] Assignee: The Procter & Gamble Company, Cincinnati, Ohio

[21] Appl. No.: 430,103

[22] Filed: Apr. 27, 1995

Related U.S. Application Data

[63] Continuation of Ser. No. 168,434, Dec. 20, 1993.

[51] Int. Cl.$^6$ ....................................................... C08K 5/49
[52] U.S. Cl. .......................... 524/115; 524/127; 524/128; 524/143; 524/145; 524/414; 524/456; 524/500; 524/539; 525/437; 525/439; 528/176
[58] Field of Search .................................... 524/115, 127, 524/128, 143, 145, 414, 456, 500, 539; 525/437, 439; 528/176

[56] References Cited

U.S. PATENT DOCUMENTS

| | | | |
|---|---|---|---|
| 1,683,347 | 9/1928 | Gray et al. | 536/72 |
| 1,698,049 | 1/1929 | Clarke et al. | 536/63 |
| 1,880,560 | 10/1932 | Webber et al. | 536/69 |
| 1,880,808 | 10/1932 | Clarke et al. | 536/63 |
| 1,984,147 | 12/1934 | Malm | 536/82 |
| 2,129,052 | 9/1938 | Fordyce | 536/76 |
| 3,332,926 | 7/1967 | Barron, Jr. et al. | 525/366 |
| 3,480,016 | 11/1969 | Costanza et al. | 604/366 |
| 3,550,592 | 12/1970 | Bernardin | 604/366 |
| 3,585,257 | 6/1971 | Mueller, Jr. et al. | 525/114 |
| 3,617,201 | 11/1971 | Berni et al. | 8/120 |
| 3,707,430 | 12/1972 | Costanza et al. | 428/169 |
| 3,840,512 | 10/1974 | Brackman | 524/287 |
| 3,860,003 | 1/1975 | Buell | 604/385.2 |
| 4,393,167 | 7/1983 | Holmes et al. | 525/64 |
| 4,440,889 | 4/1984 | Hergenrother et al. | 524/143 |
| 4,489,056 | 12/1984 | Himmelstein et al. | 424/486 |
| 4,695,278 | 9/1987 | Lawson | 604/385.2 |
| 4,780,319 | 10/1988 | Zentner et al. | 424/476 |
| 4,797,468 | 1/1989 | De Vries | 528/354 |
| 4,808,178 | 2/1989 | Aziz et al. | 604/385.2 |
| 4,816,025 | 3/1989 | Foreman | 604/385.2 |
| 4,880,592 | 11/1989 | Martini et al. | 264/514 |
| 4,929,711 | 5/1990 | Chang et al. | 528/220 |
| 4,944,734 | 7/1990 | Wallach | 604/358 |
| 4,957,997 | 9/1990 | Chang et al. | 528/220 |
| 4,962,135 | 10/1990 | Braeken et al. | 523/122 |
| 4,983,651 | 1/1991 | Griffin | 524/47 |
| 5,053,482 | 10/1991 | Tietz | 528/272 |
| 5,124,421 | 6/1992 | Ulbrich et al. | 526/212 |
| 5,142,023 | 8/1992 | Gruber et al. | 528/354 |
| 5,151,092 | 9/1992 | Buell | 604/385.2 |
| 5,171,308 | 12/1992 | Gallagher et al. | 604/372 |
| 5,234,977 | 8/1993 | Bastioli et al. | 524/47 |

FOREIGN PATENT DOCUMENTS

| | | |
|---|---|---|
| 0527447A1 | 8/1992 | European Pat. Off. . |
| 1103650 | 7/1989 | Japan . |
| 1434641 | 5/1976 | United Kingdom . |
| WO90/01521 | 2/1990 | WIPO . |
| WO90/10671 | 9/1990 | WIPO . |
| WO91/02015 | 2/1991 | WIPO . |
| WO92/09654 | 6/1992 | WIPO . |
| WO93/00399 | 11/1993 | WIPO . |

OTHER PUBLICATIONS

Controlled Release from Erodible Poly(ortho ester) Drug Delivery System, Sparer et al., Journal of Controlled Release, I(1984) 23–32.
In Vitro and In Vivo Release of Levonorgestrel from Poly-(ortho esters), J. Heller et al., Journal of Controlled Release, I (1985) 233–238.
Union Carbide Brochure F–60456 "Tone Polymers," 1988.
"Polymer Handbook, 3rd Ed.," Brandrup & Immergut, J. Wiley & Sons, §VI, pp. 56–67.
Modern Plastics Encyclopedia, pp. 23–24 (McGraw Hill 1990).
"The Prospects for Biodegradable Plastics," F. Rodriguez (ChemTech, Jul. 1971).
Industrial Bioprocessing, L. Koshan, May 1992; pp.1–2.
CRC Handbook of Chemistry & Physics, 73rd Ed., CRC Press, Section 8, p. 43.
The Biocycle Guide to the Art & Science of Composting, J6 Press, 1991, pp. 14–27.
Plastics Extrusion Technology—2d Ed., Allan A. Griff, (Van Nostrand Reinhold, 1976) pp. 129–171.
Modern Plastics, Aug. 1989, pp. 48–53, Klemchuk, Peter P.
PHBV Biodegradable Polyester, Business 2000+/Winter 1990, pp. 11–13, T. J. Galvin.
Polymer Degradation, Principles & Practical Applications, W. Schnabel, pp. 166–167.
Technical Data Sheet, Bionolle Polyester/Biodegradable Aliphatic Polyester, Showa High Polymer Co., Ltd.

Primary Examiner—Samuel A. Acquah
Attorney, Agent, or Firm—Bart S. Hersko; E. Kelly Linman; Jacobus C. Rasser

[57] ABSTRACT

Polymer compositions having enhanced biodegradability are disclosed. The compositions comprise a blend of:

(1) a polymer containing hydrolyzable bonds; and (2) a substantially water-insoluble, pH-modifying compound capable of accelerating the hydrolysis of the hydrolyzable bonds in the polymer.

The invention also relates to polymer films comprising such compositions and absorbent articles containing such polymer compositions or films. The compositions are particularly suitable for use in disposable absorbent articles such as diapers.

2 Claims, No Drawings

PH-MODIFIED POLYMER COMPOSITIONS WITH ENHANCED BIODEGRADABILITY

This is a continuation of application Ser. No. 08/168,434, filed on Dec. 20, 1993.

TECHNICAL FIELD

The present invention relates to biodegradable polymeric compositions and, more particularly, polymeric compositions having enhanced biodegradability relative to the polymer itself. Films prepared from such compositions are particularly suitable for use as backsheets in disposable absorbent articles designed for absorbing various bodily fluids, such as diapers, training pants, sanitary napkins, pantiliners, and the like.

BACKGROUND OF THE INVENTION

A wide variety of disposable absorbent structures designed for the absorption of bodily fluids, such as urine and menses, are known. Such products generally comprise some sort of fluid-permeable topsheet material, an absorbent core, and a fluid-impermeable backsheet material. The bulk of such products is often the absorbent core component, such that a typical disposable diaper having an absorbent core consisting primarily of wood pulp fibers consists of about 80% biodegradable materials. However, the remaining components generally comprise materials which are typically considered to be non- or marginally- biodegradable. For example, topsheet and backsheet materials are often prepared from polypropylene or polyethylene.

The biodegradability of disposable absorbent products has recently been emphasized. Although these disposable products typically largely comprise materials that would be expected to ultimately biodegrade, and although such products contribute only a very small percentage of the total solid waste materials generated by consumers each year, there is nevertheless a currently perceived need to devise such disposable products from materials that biodegrade relatively quickly, thereby lessening their bulk. There is a particular need to replace polyethylene backsheets with liquid impervious, biodegradable films since the backsheet is typically the largest non-biodegradable component of an absorbent article. To avoid a buildup of man-made materials in the soil, it is desirable that such materials be fully biodegradable, i.e., biodegradation is complete to carbon dioxide, water, biomass, minerals, and optionally methane. It is further desirable that biodegradation occur as rapidly as possible, in order to avoid the accumulation of man-made materials in the soil. It is also desirable that these biodegradable materials be compostable.

Microbial degradation of "natural" polymers such as starch, cellulose, and lignin typically involves an initial hydrolysis of the polymer by extracellular enzymes (enzymatic hydrolysis). The resultant monomers or low molecular weight oligomers can be internalized and subsequently metabolized by a variety of intracellular enzymes.

Various synthetic polymers for use in disposable absorbent articles have been described as biodegradable. For example, International Publication No. WO 92109654 describes aliphatic-aromatic copolyesters derived from dicarboxylic acids or derivatives thereof and aliphatic diols, and binary blends of cellulose esters with aliphatic-aromatic copolyesters. Polymeric compositions comprising a destructurized starch component and a polymeric component consisting of a blend of hydroxyacid polymers and ethylene-vinyl alcohol or polyvinyl alcohol are disclosed in International Publication No. WO 90/10671. The preparation of polyesters based upon copolymerization of polyethylene terephthalate and non-aromatic diacids such as adipic and glutaric acids with sulfoisophthalic acid derivatives are described in U.S. Pat. No. 5,171,308 and the associated parent applications.

Although the above polymer materials may meet certain requirements for composting (e.g., facile physical fragmentation with ultimate loss of macroscopic structural integrity), the ability to completely biodegrade to carbon dioxide, water, biomass, minerals, and optionally methane within a period of time comparable to materials which are generally recognized as biodegradable and compostable, such as yard waste, has yet to be demonstrated. In particular, synthetic polymers such as aromatic-aliphatic copolyesters are not readily biodegradable because microbes have not yet evolved with the requisite extracellular enzymes to generate low molecular weight oligomers and/or monomers which can be metabolized. Therefore, there is a continuing need to enhance both the degree (i.e., the extent) and rate of biodegradation of such polymeric materials.

Toilet-flushable sanitary products containing binder resins that are degradable in toilet water upon the addition of water-soluble acids or bases to the toilet water have been disclosed. See, for example, U.S. Pat. No. 3,480,016 issued to Costanza et al., on Nov. 25, 1969 and U.S. Pat. No. 3,707,430 issued to Costanza et al., on Dec. 26, 1972. However, these patents do not describe the incorporation of the acids or bases into a polymer film. Indeed, the incorporation of such water-soluble acids and bases is believed to be unsuitable for forming polymer films and, more particularly, polymeric films for use in absorbent products intended for applications involving human contact, such as diapers. This is because such water-soluble acids and bases are strong acids and bases. It is believed that the incorporation of such materials into film products would present problems in manufacturing such as equipment corrosion, safety concerns, and moisture sensitivity. It is also believed that the incorporation of such materials into a polymer may result in premature hydrolysis of the polymer composition due to the hygroscopic character of such materials combined with their inherent acidity or basicity. Thus, such a composition may not be sufficiently stable for its intended use. This may be a particular problem in applications where the composition is exposed to moisture for extended periods, such as may occur with the overnight wearing of diapers. Such products may not retain sufficient integrity to satisfy consumer needs. In addition, the presence of strong acids and bases in components of absorbent articles wherein contact with human skin may occur presents toxicity concerns.

Thus there remains a need for film-processable polymers which are suitable for use in disposable absorbent articles and which have enhanced biodegradability. It is therefore an object of the present invention to provide biodegradable polymers which have increased rates of biodegradability. Another object of the invention is to provide such polymers which are fully biodegradable to carbon dioxide, water, biomass, and minerals. An additional object is to provide such materials which are non-toxic to humans and which remain sufficiently stable during use. Another object is to provide polymer materials which are compostable. Additional objects include providing disposable absorbent articles having enhanced biodegradability.

SUMMARY OF THE INVENTION

The present invention is directed to polymer compositions having enhanced biodegradability. The polymer compositions comprise a polymer containing hydrolyzable bonds and a substantially water-insoluble, pH-modifying compound such as a substantially water-insoluble acid or base. In a preferred embodiment the polymer composition comprises a polymer containing base-hydrolyzable bonds and a substantially water-insoluble, pH-modifying basic compound. The present invention also relates to polymer films comprising these polymer compositions and absorbent articles containing the polymer compositions or films. The films are particularly suitable for use as backsheets in disposable absorbent articles such as diapers, training pants, sanitary napkins, and adult incontinence devices.

The rate of biodegradation of polymer compositions derived from high molecular weight synthetic and natural polymers containing hydrolyzable bonds can be enhanced by the incorporation of the substantially water-insoluble, pH-modifying compound into the polymer. Without wishing to be bound by theory or to limit the invention, it is believed that the biodegradation of such high molecular weight polymers according to the invention involves an initial, hydrolytic degradation step. This step involves chemical (non-enzymatic) hydrolysis of the hydrolyzable bonds in the polymer and is believed to be the rate-limiting step in the overall biodegradation process. Upon exposure to hydrolysis conditions (moisture and optionally heat), the pH-modifying compound serves to catalyze this initial chemical hydrolysis, resulting in polymer molecular weight reductions approaching 1004old. Monomers and/or oligomers which have a molecular weight ranging from about 100 to about 10,000 grams/mole, preferably from about 100 to about 1,000 grams/mole, are typically formed in this step. In the second, microbial degradation step, microbes assimilate and enzymatically metabolize these low molecular weight residues. It is believed that the low molecular weight residues are more readily metabolized by microorganisms than the original polymer. Thus, the overall rate and extent of biodegradation of such polymers and products incorporating the same are enhanced.

DETAILED DESCRIPTION OF THE INVENTION

The polymer compositions of the invention comprise a polymer containing a functional group containing at least one hydrolyzable bond. "Polymer" is intended to include homo- and co- polymers and blends thereof. (a copolymer or blend includes at least one other polymer which may or may not contain hydrolyzable bonds). By "hydrolyzable," "hydrolysis," and the like is meant the ability of water to chemically react with a substance to form two or more new substances. This involves ionization of the water molecule as well as splitting of the compound being hydrolyzed, e.g., an ester group of a polyester is hydrolyzed into the corresponding carboxylic acid and alcohol. By "acid-hydrolyzable bonds" and "base-hydrolyzable bonds" it is meant that the hydrolysis of the bond is initiated or catalyzed by an acidic or basic material, respectively. A bond may be both acid and base hydrolyzable. In addition, both types of bonds may be present in the polymer. The functional group containing hydrolyzable bonds may be present in the linear portions of the polymer chain (i.e., internal groups) or may be pendant to the polymer chain.

Exemplary functional groups which contain acid-hydrolyzable bonds include ortho-ester and amide groups. Exemplary functional groups which contain base-hydrolyzable bonds include α-ester and anhydride groups. Functional groups which contain both acid- and base- hydrolyzable bonds include carbonate, ester, and iminocarbonate groups. Thus, exemplary polymers for use in the polymer compositions of the invention include polyesters, cellulose esters, polyester polyurethanes, polyamides, polycarbonates, and polyamino acids. For economic and functional reasons, the polymer is preferably a polyester.

Polyesters for use as the base polymer in the present invention may be aliphatic, aromatic, or mixed aliphatic and aromatic. Typically the polyester will be aliphatic or mixed aliphatic and aromatic.

Exemplary aliphatic polyesters include polycaprolactone, polyesters derived from the reaction of an aliphatic dicarboxylic acid and a diol, polyhydroxyalkanoates, and oxidized ethylene/carbon monoxide polymers.

Polycaprolactone can be produced, e.g., via the ring-opening polymerization of epsilon-caprolactone. Such polymers are available from the Union Carbide Corporation under the tradename TONE in a variety of molecular weight (hereinafter MW) grades. For example, TONE polymer P-300, P-700, P-767 and P-787 have average molecular weights of about 10,000; about 40,000; about 43,000; and about 80,000 grams per mole, respectively. These polymers are described in Union Carbide Brochure F-60456 entitled "Tone Polymers," incorporated herein by reference. Polycaprolactone polymers having molecular weights of at least about 40,000 grams per mole can be melt processed into strong, water resistant films and are therefore generally preferred for use in disposable film applications. Polycaprolactone polymers having an average molecular weight of about 80,000 grams per mole are especially preferred.

Block copolymers of polycaprolactone with polydienes such as polyisoprene and polybutadiene are also suitable for use in the present invention. Such polyesters are described in U.S. Pat. No. 3,585,257, issued to Mueller et al., incorporated herein by reference. The block copolymers can have various architectures, for example, an A-B diblock copolymer, an A-B-A triblock copolymer, and —(A-B)—multi-block copolymers where n=2, 3, etc.

Another type of aliphatic polyester suitable for use in the present invention are those polyesters derived from the reaction of an aliphatic dicarboxylic acid and a diol, for example, as described in "An Overview of Plastics Degradability," Klemchuk, *Modern Plastics*, (August, 1989), incorporated herein by reference. Examples of these types of aliphatic polyesters include polyethylene adipate, poly (1,3-propanediol adipate), poly (1,4-butanediol adipate), poly (1,4-butanediol sebacate), poly (1,3-propanediol succinate), and poly (1,4-butanediol glutarate). Such copolymers are commercially available from, for example, Showa Highpolymer Co., Ltd. under the tradename BIONOLLE.

Suitable aliphatic polyesters also include the polyhydroxyalkanoates such as those derived from hydroxyalkanoic acids. Polyhydroxyalkanoates include synthetic polymers such as polylactides derived from lactic acid and bacteria-derived polymers such as polyhydroxybutyrate (PHB) polymers and polyhydroxybutyrate/valerate (PHBV) copolymers. Preferred examples of polylactides are described in U.S. Pat. No. Nos. 5,142,023 and 4,797,468 and in International Publication No. WO 90/01521, each of which is incorporated herein by reference. Preferred examples of PHB homopolymer and PHBV copolymers are described in U.S. Pat. No. 4,393,167, issued to Holmes et al. on Jul. 12, 1983, and U.S. Pat. No. 4,880,592, issued to Martini et al. on Nov. 14, 1989, both references being incorporated herein by reference. Such copolymers are commercially available from Imperial Chemical Industries under the tradename BIOPOL. These polymers are produced from the fermentation of sugar by the bacterium Alcaligenes eutrophus and are discussed in Business 2000+, (Winter, 1990), incorporated herein by reference.

Other types of aliphatic polyesters suitable for use herein are the oxidized ethylene/carbon monoxide polymers such as described in U.S. Pat. Nos. 4,929,711 and 4,957,997; each incorporated herein by reference, and polymers such as polyethylene sebacate, polyethylene succinate, and polyhexamethylene sebacate. Further examples of suitable aliphatic polyesters are found in "Polymer Handbook, Third Edition", J. Brandrup and E. H. Immergut, John Wiley & Sons, Section VI, pp. 56–67, incorporated herein by reference.

Mixed aliphatic and aromatic polyesters include, for example, those produced by random copolymerization of polyethylene terephthalate (i.e., PET) or polybutylene terephthalate (i.e., PBT) with aliphatic constituents. For example, U.S. Pat. No. 5,053,482, issued to Tietz on Oct. 1, 1991, describes polyesters based on polyethylene terephthalate (PET) copolymerized with diethylene glycol and 5-sulfoisophthalic acid. International Patent Application WO 91/02015, published Feb. 21, 1991, discloses hydrodegradable, random copolymers comprised of aromatic polyesters such as PET or PBT randomly interrupted with aliphatic hydrodegradable link polymers such as polyglycolic acid, polylactic acid, polycaprolactone, polyhydroxybutyrate, polyhydroxybutyrate/valerate, polybutylene oxalate, polyethylene adipate, polyethylene carbonate, polybutylene carbonate, and other polyesters containing silyl ethers, acetals, or ketals. Each of these references is incorporated herein by reference.

Other mixed aliphatic and aromatic polyesters include copolymers derived from aromatic monomers and aliphatic monomers such as oxalates, malonates, succinates, glutarates, adipates, pimelates, suberates, azelates, sebacates, nonanedioates, glycolates, and mixtures thereof. Such copolymers may contain PET or PBT.

Cellulose esters represent another type of polymer suitable for use in the present invention. Such esters are described in Modern Plastics Encyclopedia, p.p. 23–24 (McGraw Hill, 1990), incorporated herein by reference. The cellulose esters useful in the present invention can be prepared using techniques known in the art or are commercially available, e.g., from the Eastman Chemical Company, Inc., Kingsport, Tenn., U.S.A. The cellulose esters which are particularly useful in the present invention have degrees of substitution (DS) in the range of from about 1.6 to about 3.0. Preferred cellulose esters include cellulose acetate (CA), cellulose propionate (CP), cellulose butyrate (CB), cellulose acetate propionate (CAP), cellulose acetate butyrate (CAB), cellulose propionate butyrate (CPB), and the like. More preferably, the cellulose ester is CAP or CAB, and is most preferably CAP. These cellulose esters are described in U.S. Pat. Nos. 1,698,049; 1,683,347; 1,880,808; 1,880,560; 1,984,147; 2,129,052; and 3,617,201; each being incorporated herein by reference.

Polyester polyurethanes suitable for use herein include, for example, biodegradable polyurethanes prepared from low molecular weight aliphatic polyesters derived from epsilon-caprolactone or the reaction products of a dioldicarboxylic acid condensation. For example, biodegradable polyester urethanes derived from polyethyleneglycol adipate, poly (1,3-propanediol adipate) and poly (1,4-butanediol adipate) are disclosed in "The Prospects for Biodegradable Plastics", F. Rodriguez (*Chem Tech*, July - 1971), incorporated herein by reference. Exemplary aliphatic polyester urethanes are available from Morton International, Inc. under the tradename MORTHANE.

Suitable polyamides for use in the present invention include, for example, copolymers comprising α-amino acids and ε-aminoalkanoic acids, for example, glycine and ε-aminocaproic acid. Other suitable polyamides include polyamide-esters and polyamide-urethanes derived from amino alcohols. Such polymers and methods of making the same are known in the art.

Polycarbonates for use in the present invention include, for example, the polyesters comprising bisphenol-A or hydroquinone and selected carboxylic acids. Exemplary materials are described in *Polyesters*, Korshak and Vinogradova, Pergamon Press Oxford (1965), p.p. 448–517, incorporated herein by reference.

Polyamino acids for use in the present invention include, for example, bacteria-derived poly(γ-glutamic acid) and polyaspartic acid. Polyaspartic acid may be particularly useful as a replacement for polyacrylic acid as an absorbent or a dispersant. Polyaspartic acid is described in *Industrial Bioprocessing*, L. Koshan, (May 1992): 1–2, incorporated herein by reference.

The polymer composition further comprises a substantially water-insoluble, pH-modifying compound. By "pH-modifying" is meant the ability of the compound to change the pH of an aqueous environment when the compound is placed in or dissolved in that environment. The pH-modifying compound is capable of accelerating the hydrolysis of the hydrolyzable bonds in the polymer upon exposure of the polymer composition to moisture and optionally heat. By "substantially water-insoluble" it is meant that the compound has a solubility product or room temperature solubility as described herein. Suitable substantially water-insoluble pH-modifying compounds include substantially water-insoluble acids and bases. Inorganic and organic acids or bases may be used.

Suitable basic compounds have a 25° C. solubility product constant in water of from about $1 \times 10^{-6}$ to $1 \times 10^{-13}$. The solubility product constant is defined, along with the constants for various compounds, in *CRC Handbook of Chemistry and Physics*, 73rd Ed., CRC Press, p.8–43, incorporated herein by reference.

Suitable inorganic bases include, for example, alkaline earth metal salts, alkaline earth metal oxides, alkali metal salts of organic acids, and basic mono-, di-, and tri- phosphates. Suitable organic bases include, for example, the conjugate bases of organic acids such as the organic, acidic pH-modifying compounds described herein. Exemplary bases include calcium oxide, calcium hydroxide, magnesium oxide, magnesium hydroxide, basic mono-, di-, and triphosphates, potassium and sodium stearate, and calcium tartrate. The basic compound is preferably calcium oxide, calcium hydroxide, magnesium oxide, magnesium hydroxide, or any mixture thereof.

Suitable acidic compounds have a room temperature (i.e., 25° C.) solubility in water of less than 10 g/l. Suitable acidic compounds include, for example, organic acids such as aliphatic, aromatic, and mixed aliphatic/aromatic acids (e.g., aliphatic, aromatic, and mixed aliphatic/aromatic carboxylic acids), and inorganic acids such as acid phosphates. Exemplary organic acids are valeric, isovaleric, caproic, heptanoic, lauric, palmitic, adipic, citric (monohydrate), benzoic, 2-acetoxybenzoic, and phthalic acid. Inorganic acids include, for example, mono-, di-, and tri- acid phosphates. The acidic compound is preferably citric acid, adipic acid, phthalic acid, an acid phosphate, or any mixture thereof.

The level of pH-modifying compound used in the polymer composition may be varied by one of ordinary skill in the art to minimize or eliminate any potential skin sensitivity or to maximize hydrolytic activity. Typically, the pH-modifier will be used at a level of from about 1 to about 15 percent based on the weight of the polymer containing hydrolyzable bonds. Hydrolyric activity tends to increase with increasing levels of the pH-modifying compound.

Any combination of an acidic compound and a polymer having acid-hydrolyzable bonds, or a basic compound with a polymer having base-hydrolyzable bonds may be used. However, the combination should provide both sufficient stability of the polymer in storage and in the intended application, and an improved rate of biodegradability under disposal conditions such as in a landfill or in a composter. Thus, the particular blend is preferably chosen such that the polymer composition does not prematurely decompose while in its intended use, for example, when in contact with bodily fluids. The particular selection should also provide an increased rate of biodegradability relative to the unmodified polymer. In general, the components should be selected such that hydrolysis does not occur to a significant extent under the normal storage and use conditions of the composition. These conditions may range, for example, between the extremes of hot and arid, hot and humid, exposure to urine for extended times (e.g., greater than 16 hours), and the extremes of cold and arid or cold and humid. In general, hydrolysis of the polymer composition under normal storage and use conditions should not occur in less than about 1 day, preferably less than about 1 week. Upon later exposure to more extreme hydrolysis conditions, e.g., as may be encountered in a municipal solid waste composting process (typically relatively high moisture and optionally temperature), hydrolysis should occur to an extent sufficient to allow microbial degradation of the resultant polymer fragments.

Typically, a basic pH-modifying compound is used to accelerate the hydrolysis of a polyester polyurethane, polycarbonate, or polyamino-acid. An acidic pH-modifying compound is preferably used to accelerate the hydrolysis of a poly(ortho-ester). To accelerate the hydrolysis of a polyester, cellulose ester, or polyamide, either a basic or acidic pH-modifying compound can be used. Acids may, however, be metabolized by microbes which develop in a composter during the initial transient acidic phase of the compost process, as described in *The Biocycle Guide to the Art and Science of Composting*, JG Press, 1991, p.p. 14–27, incorporated herein by reference. This would reduce the effective concentration of acid and hence may reduce the extent of hydrolysis. Therefore, in order to enhance biodegradability in a composter, it is generally preferred to use a basic pH-modifying compound in compositions which are based primarily on a polyester, cellulose ester, and/or a polyamide.

The rate and extent of the hydrolytic step (and thus of overall biodegradation) typically depends on the ease of polymer hydrolysis, the strength of the pH-modifying compound, the number of hydrolyzable bonds in the polymer, and the hydrolysis conditions (moisture and optionally heat). The ease of hydrolysis will often vary between polymers. Generally, the lower the glass transition temperature (i.e., Tg), crystallinity, or hydrophobicity of the polymer, the more readily the polymer will be hydrolyzed. Thus, for a given concentration of a pH-modifying compound and set of hydrolysis conditions, polymers having a relatively low Tg, low crystallinity, and/or low hydrophobicity will typically have a greater rate and extent of hydrolysis than polymers having a relatively high Tg, crystallinity, and/or hydrophobicity. In general, the greater the strength of the pH-modifying compound, the greater the rate and extent of hydrolytic degradation for a given polymer, set of hydrolysis conditions, and concentration of pH-modifying compound. Similarly, for a given set of hydrolysis conditions and concentration of a pH-modifying compound, the greater the number of hydrolyzable bonds in the polymer, the greater the rate and extent of hydrolysis.

Hydrolysis conditions include moisture and, optionally, heat. For example, commercial composters typically have a moisture content of at least about 35 weight % (typically about 50 weight %) and temperatures in the range of about 25° C. to about 70° C. (typically in excess of about 40° C.) in the compost. Without intending to be bound by theory, it is believed that for a given polymer and concentration of a pH-modifying compound, the rate and extent of hydrolysis will increase with an increase in moisture in the polymer environment. It is also believed that for a given polymer composition and environmental moisture level, the rate and extent of hydrolysis tends to increase with an increase in temperature, most likely with an increase in temperature to at least the glass transition temperature of the polymer containing hydrolyzable bonds.

Typically, significant microbial degradation will only occur when a polymer or fragment thereof has a molecular weight which is sufficiently low to allow internal enzymatic microbial degradation. Thus, the rate and extent of the microbial degradation step generally depends on the average molecular weight of the polymer between hydrolyzable bonds and the rate and extent of hydrolysis occurring in the hydrolyric step. The lower the molecular weight fragments of the polymer resulting from hydrolysis, the more susceptible the fragments are to microbial attack and thus biodegradation. Typically, to achieve enhanced biodegradability in accordance with the present invention, the average molecular weight of the polymer chain between hydrolyzable bonds is less than about 1000 grams per mole, preferably less than about 500 grams per mole. Without intending to be bound by theory, it is believed that the rate and extent of microbial degradation for these polymers will increase with the rate and extent of hydrolysis. In addition, without intending to be bound by theory, it is expected that for a given degree of hydrolysis of these polymers, the rate and extent of microbial degradation increases as the average molecular weight between hydrolyzable bonds decreases.

The pH-modifying compound may be incorporated into the polymer by any known method of incorporating particulate materials into polymer materials. Such methods are well-known to those skilled in the art and include solution slurries, pre-compounding, and co-extrusion. The resultant compositions are typically dried soon after compounding in order to prevent or minimize any premature hydrolysis. In addition, the composition is preferably dried after any subsequent steps in which significant moisture contamination may occur. Drying conditions are dependent on polymer type and are readily available from the base resin manufacturer. Typically, drying is performed by subjecting the polymer or polymer composition to elevated temperatures (e.g., about 40° C.–60° C.) for a period of about 4–12 hours under vacuum or under low moisture air (dew point below about 0° F. (18° C.)). Drying temperatures are preferably selected to avoid softening and subsequent coalescence of resin particles.

The polymer compositions may optionally contain other components conventionally used in plastics compounding, including pigments and plasticizers. In polymer films, it may be particularly desirable to use conventional film processing aids such as antiblocking agents, antistatic agents, slip agents, antioxidants, and pro-heat stabilizers such as are known in the art. The use of such processing aids are described in more detail in International Publication No. WO 93/00399; "Biodegradable, Liquid Impervious Films;" Toms and Wnuk; published on Jan. 1, 1993 and incorporated herein by reference.

The compositions may also contain polymers other than a polymer containing hydrolyzable bonds, e.g., polyolefins. However, since such polymers will generally decrease the biodegradability of the polymer composition, their inclusion in compositions intended for use in disposable products is not preferred. Without intending to be bound by theory, it is also believed that heat stabilizers and primary and/or secondary antioxidants may interfere with the biodegradation of the polymer composition, particularly if they are added in relatively high levels. Without intending to be bound by theory, it is believed that any negative effect of such polymers, stabilizers, and/or antioxidants on biodegradability may be at least partially offset by the pH-modifying compound. Consequently, the present invention may provide broader film processing latitude (e.g., higher process temperatures) than was previously achievable in unmodified polymers, while still providing compositions having enhanced biodegradability.

Applications:

The resultant polymer compositions can be processed by methods such as are known in the art into various forms, e.g., coatings, free films or sheets, or other molded articles. For use in disposable products, the polymer composition will often be formed into a free film. Films may be prepared by any conventional method for producing polymer films using any conventional film making equipment. The polymer compositions are typically melt processed into films using either cast or blown film extrusion methods, both of which are described in "Plastics Extrusion Technology— 2nd. Ed.", Allan A. Griff (Van Nostrand Reinhold—1976); incorporated herein by reference; and in the above referenced and incorporated International Publication No. WO 93/00399.

The polymer composition of the present invention is particularly useful in those applications in which biodegradability is typically desired. For example, the films of the polymer composition are useful as components of disposable absorbent articles, agricultural mulch films, packaging films, garbage bags, and the like. In a preferred embodiment, the films are used as components of disposable absorbent articles, e.g., in the form of backsheets or fastener tabs.

As used herein, the term "absorbent article" refers to devices which absorb and contain bodily fluids (e.g., urine, menses, feces), and, more specifically, refers to devices which are placed against or in proximity to the body of the wearer to absorb and contain the various fluids discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, sanitary napkins, pantiliners, and the like.

Disposable diapers typically comprise a liquid pervious topsheet; a liquid impervious backsheet joined with the topsheet, an absorbent core positioned between the topsheet and the backsheet, and a fastening system. In addition, these diapers may comprise various elastic components such as elasticized side panels, elasticized leg cuffs, or an elastic waist feature. The diaper of the present invention may be assembled in a variety of well known configurations. Preferred diaper configurations are described generally in U.S. Pat. No. 3,860,003, issued to Buell on Jan. 14, 1975; and U.S. Pat. No. 5,152,092, issued to Buell, et al. on Sep. 29, 1992; each of which is incorporated herein by reference. Alternatively preferred configurations for disposable diapers herein are also disclosed in U.S. Pat. No. 4,808,178, issued to Aziz, et al. on Feb. 28, 1989; U.S. Pat. No. 4,695,278, issued to Lawson on Sep. 22, 1987; and U.S. Pat. No. 4,816,025, issued to Foreman on Mar. 28, 1989. These patents are incorporated herein by reference.

U.S. Pat. No. 5,152,092 describes in detail various components which may be present in the diaper of the present invention. In order to enhance the biodegradability of the diaper, the diaper has at least one component containing the polymer composition of the present invention. The composition can be incorporated in any form, including film, particulate (including fiber), or woven or nonwoven web form. The diaper components may also include materials heretofore used in such articles. In a preferred embodiment, the diaper comprises only biodegradable materials.

Any component of the diaper may contain the polymer composition of the present invention. Preferably, the backsheet comprises a film of the polymer composition. The polymer composition may also be incorporated into the topsheet, for example, in the form of an apertured film or a woven or nonwoven web of fibers which comprise the polymer composition. In addition, the fastening system, e.g., tape tabs, may comprise the polymer composition. The absorbent core can also contain the polymer composition. A composition having polyaspartic acid as a base polymer may be particularly suitable for use in the absorbent core. Stretchable components, e.g., elasticized leg cuffs, an elastic waistband, and elastic side panels can contain the polymer composition. For stretch applications, the polymer composition preferably comprises an elastomeric, aliphatic polyester based polyurethane.

The polymer compositions of the invention have enhanced biodegradability, and generally enhanced compostability, relative to the unmodified (i.e., "base") polymer. Thus, products incorporating the polymer composition and absorbent articles comprising such compositions and/or products also have enhanced biodegradability, and generally enhanced compostability. Therefore, although the following description is directed to the polymer composition, it should be clear that it applies in a similar manner to such products and absorbent articles.

As used herein, "biodegradable," "biodegradability," and the like means the capability of undergoing natural processes in which a material is broken down by metabolic processes of living organisms, principally fungi and bacteria. In the presence of oxygen (aerobic biodegradation), these metabolic processes yield carbon dioxide, water, biomass, and minerals. Under anaerobic conditions (anaerobic biodegradation), methane may additionally be produced.

By "enhanced biodegradability" it is meant that the rate of biodegradation is increased relative to the unmodified polymer. Enhancement may also include an increased extent of biodegradation, which in turn refers to the degree to which the polymer or product is broken down by the living organisms. The extent of biodegradation refers to the degree to which the material is converted to carbon dioxide, water, biomass, and minerals (under aerobic conditions), and optionally also methane (under anaerobic conditions). "Fully biodegradable" materials are converted completely to carbon dioxide, water, biomass, and minerals (under aerobic conditions), and optionally also methane (under anaerobic conditions).

Biodegradation, and thus any enhancements thereof, can be established by a modified Sturm test or by an Organic Waste System (i.e., OWS) method. The modified Sturm test is a dilute, aqueous, aerated test. The OWS method is a controlled composting biodegradation test. Both tests are based on the fact that during the aerobic biodegradation of organic materials, carbon dioxide is the primary carbon-containing decomposition product which is generated. The cumulative $CO_2$ production can be determined by monitoring and integrating the evolved $CO_2$ in the exhaust stream from a test reactor. The percentage biodegradation can then be calculated as the percentage of carbon in the test material (determined by standard physico-chemical methods) which is converted to $CO_2$. The Sturm test employs an inoculum derived from the supernatant of a settled, activated sludge from a waste water treatment facility. The inoculum in the OWS test consists of a mature, stabilized fraction of municipal solid waste. Details of these techniques are found in "Ready Biodegradation: Modified Sturm Test;" OECD Method #301B; and in "Standard Test Method for Determining Aerobic Biodegradation of Plastic Materials under Controlled Composting Conditions," ASTM Method #D5338-92; each test method being incorporated herein by reference.

A material may be biodegradable without being compostable. "Compostability," "compostable," and the like means the ability of a material to undergo physical, chemical, thermal, and/or biological degradation in a municipal solid waste (hereinafter "MSW") composting facility such that the material will break down into, or otherwise become part of, usable finished compost. To be considered compostable, a material must also ultimately fully biodegrade in the environment in a manner similar to paper and yard waste.

Municipal solid waste (MSW) composting processes generally involve three sequential phases: waste preparation, active composting, and curing. During the waste preparation phase, raw MSW is first sorted to remove recyclables and known non-compostable materials. The sorted materials are then reduced in physical size, generally via a grinder or rotating drum such as are known in the composting art. The goal is to obtain a consistent physical size, typically particles of about 2" diameter, which will maximize surface area for microbial attack and allow effective air management during the subsequent active composting phase. Following size reduction, materials are usually screened through a 1.5"–2" screen. In order to be compostable by this process, a material must be capable of being reduced in size such that it passes through this screen. The rejected (>1.5"–2") fraction is typically landfilled.

Although size reduction via grinder is largely independent of the relative chemical or biological degradability of a material, the rotating drum technology offers opportunities for engineered material characteristics that promote size reduction. The rotating drum process is microbiologically active with a duration of several days, typically 3 days. During the process, free moisture is available (at least about 35% w/w, typically 50% w/w), an acidic environment develops (pH 4.5–5.5), and the temperature increases (typically to from about 40° C. to about 50° C.). Hydrolytically unstable materials often degrade in this environment such that their physical integrity is compromised and they pass the 1.5"–2" barrier.

In the active composting phase, the size-reduced materials from the waste preparation phase are arranged into self-insulating configurations, such as piles or trenches. The mass is kept moist (at least about 35% w/w moisture, typically about 50% w/w moisture), is periodically mixed to distribute nutrients and expose new surfaces for microbial attack, and is force-aerated to supply oxygen and to control temperature. The waste serves as physical support as well as a source of organic and inorganic nutrients for indigenous microbes. The major form of metabolism is aerobic respiration. One of the metabolic by-products, heat, tends to be retained within the matrix, causing self-heating. Temperatures commonly reach 70° C. or higher. At the beginning of active composting, the pH is typically acidic but can increase to as high as 8.5 by the completion of this portion of the process. Further degradation, both chemical and biological, takes place during this phase and typically results in further size reduction. After several weeks of active composting (typically 5–7 weeks), the mass is screened through the final size barrier, a ⅜"–½" screen. In order to be compostable by this process, the material must be capable of being made to pass through this screen. Rejects (>⅜"–½") from this separation step are typically landfilled.

The final phase, curing, requires the least intervention. Although many complex organic materials, including biodegradable synthetic polymers, continue to degrade after curing, this phase marks the final step of the managed composting process prior to utilization. In this phase, static piles of the actively composted material sit undisturbed for a period of several weeks to a few months. During this phase, mesophilic microorganisms as well as microfauna colonize the compost. As organic substrate availability decreases, microbial activity decreases and self-heating subsides. In order to be compostable by this process, the material must form an integral part of the usable finished compost and ultimately completely biodegrade in the environment in a manner and at a rate consistent with materials such as paper and yard waste.

"Enhanced compostability" means either rendering a previously non-compostable material compostable as defined herein, or decreasing the time required to compost an already compostable material. Enhancements in compostability of the polymer compositions of the present invention can be determined by a direct comparison of the composting processes for different materials.

The following example illustrates the practice of the present invention but is not intended to be limiting thereof.

EXAMPLE

A polymer composition which is a 95%/5% by weight blend of (a) a polyester polymer such as described in U.S. Pat. No. 5,171,308 or International Publication No. WO 92/09654 and (b) calcium hydroxide as the pH-modifying compound may be prepared as follows:

The polyester polymer is dried in a vacuum oven so as to minimize molecular weight loss of the polyester due to hydrolysis in the elevated temperature of the extruder. Sufficient drying depends on the specific polyester involved, as would be understood by the skilled artisan. Typically sufficient drying is achieved after 4 hours at 140° F. (60° C.). In 200 gram batches, 190 grams of the dried polyester and 10 grams of Ca(OH)$_2$ are melt compounded in a Rheomix TW-100 twin screw extruder (available from Haake) equipped with conical barrels, two partially intermeshing counter-rotating screws and a horizontal rod die having a 0.125 inch (0.3175 cm) diameter nozzle. The temperature of the extruder is varied from 284° F. (140° C.) in the first heating zone, to 302° F. (150° C.) in the second zone, and to 320° F. (160° C.) at the discharge end near the die. The die is maintained at 266° F. (130° C.). The screw speed is held constant at 30 rpm. The resultant, extruded molten strand is then cooled and solidified in a water bath prior to entering a Berlyn Model PEL-2 pelletizer (available from the Berlyn Co.) where it is chopped into pellets approximately 0.125 inches (0.3175 cm) long. Successive 200 gram batches are melt compounded until a total of about 1600 grams of pellets is obtained. The cooled pellets are dried as described above in order to minimize premature hydrolysis of the polymeric composition.

A film of the polymer composition is prepared as follows. A cast film is produced from the pellets using a Rheomix Model 202 0.75 inch (1.905 cm) diameter single screw extruder (available from Haake) equipped with a 6 inch (15.24 cm) wide horizontal sheet die utilizing a 0.04 inch (0.1016 cm) die gap. A constant taper screw having a 20:1 length to diameter ratio and a 3:1 compression ratio is typically employed. The temperature of the first and second heating zones is maintained at 370° F. (188° C.), and the die is maintained at 340° F. (171° C.). The screw speed is held constant at 30 rpm. The resultant molten film is passed from the die to a Postex sheet take-off system which is cooled to room temperature and then collected on a cardboard core. The take-off speed is adjusted to provide a film about 4 inches (10.16 cm) wide and 0.002 inches (50.8 microns) thick.

The resultant polymeric film will have enhanced biodegradability.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A polymer composition having enhanced biodegradability, comprising a blend of:

(i) a polycarbonate polymer containing base-hydrolyzable bonds, wherein said polycarbonate is a polyester comprising bisphenol-A and a carboxylic acid or a polyester comprising hydroquinone and a carboxylic acid;

and (ii) at least about 1%, based on the weight of the polycarbonate polymer containing base-hydrolyzable bonds, of a substantially water-insoluble, pH-modifying basic compound having a 25° C. solubility product constant in water of from about $1 \times 10^{-6}$ to about $1 \times 10^{-13}$.

2. A polymer composition having enhanced biodegradability, comprising a blend of:

(i) a polyamino acid polymer containing base-hydrolyzable bonds, wherein said polyamino acid is poly(γ-glutamic acid) or polyaspartic acid;

and (ii) at least about 1%, based on the weight of the polyamino acid polymer containing base-hydrolyzable, bonds, of a substantially water-insoluble, pH-modifying basic compound having a 25° C. solubility product constant in water of from about $1 \times 10^{-6}$ to about $1 \times 10^{-13}$.

\* \* \* \* \*